US008836778B2

(12) United States Patent
Ignatovich et al.

(10) Patent No.: US 8,836,778 B2
(45) Date of Patent: Sep. 16, 2014

(54) PORTABLE FUNDUS CAMERA

(75) Inventors: Filipp V. Ignatovich, Rochester, NY (US); David M. Kleinman, Rochester, NY (US); Christopher T. Cotton, Honeoye Falls, NY (US); Todd Blalock, Penfield, NY (US)

(73) Assignee: Lumetrics, Inc., Rochester, NY (US)

( * ) Notice: Subject to any disclaimer, the term of this patent is extended or adjusted under 35 U.S.C. 154(b) by 0 days.

(21) Appl. No.: 13/512,336

(22) PCT Filed: Dec. 4, 2010

(86) PCT No.: PCT/US2010/059000
§ 371 (c)(1),
(2), (4) Date: Aug. 1, 2012

(87) PCT Pub. No.: WO2011/069137
PCT Pub. Date: Jun. 9, 2011

(65) Prior Publication Data
US 2012/0287255 A1    Nov. 15, 2012

Related U.S. Application Data

(60) Provisional application No. 61/266,564, filed on Dec. 4, 2009.

(51) Int. Cl.
H04N 7/18 (2006.01)
A61B 3/113 (2006.01)
A61B 3/14 (2006.01)
G06K 9/00 (2006.01)

(52) U.S. Cl.
CPC .................. *A61B 3/113* (2013.01); *A61B 3/145* (2013.01); *G06K 9/00604* (2013.01)
USPC ................................................ 348/78; 348/77

(58) Field of Classification Search
CPC .... A61B 3/113; A61B 3/145; H04N 5/23219; G06K 9/00604; G06K 9/00597
USPC ....................................................... 348/65–78
See application file for complete search history.

(56) References Cited

U.S. PATENT DOCUMENTS 3,944,341 A    3/1976   Pomerantzeff
4,023,189 A    5/1977   Govignon
5,032,020 A    7/1991   Robert (Continued)

OTHER PUBLICATIONS

E.Dehoog et al., "Fundus Camera Systems: a comparative analysis," Appl. Opt. Jan. 10, 2009; 48(2): 221-228, US. EFS file name: 20130430_13-512336_IDS_NPL_Cite1.

(Continued)

*Primary Examiner* — Andy Rao
(74) *Attorney, Agent, or Firm* — John M. Hammond; Patent Innovations LLC

(57) ABSTRACT

A portable hand-held camera for imaging the fundus of an eye, the camera comprising a housing comprising an internal cavity terminating at a forward housing end, a forward lens, and a light source configured to direct light from locations distributed around the perimeter of the forward lens forwardly out of the housing end. In other embodiment, a portable hand-held camera for imaging the fundus of an eye includes optics configured to focus light reflected back from the fundus onto an image receptor, with the optics being capable of varying the field of view among differing portions of the fundus. Methods to ensure unique image identification and storage are described.

12 Claims, 11 Drawing Sheets

(56) References Cited

U.S. PATENT DOCUMENTS

| | | | |
|---|---|---|---|
| 5,481,653 | A | 1/1996 | Kashiwagi et al. |
| 5,822,036 | A | 10/1998 | Massie et al. |
| 6,065,837 | A | 5/2000 | Goldfain et al. |
| 7,364,297 | B2 | 4/2008 | Goldfain et al. |
| 2004/0246595 | A1 | 12/2004 | Beach |
| 2008/0231803 | A1 | 9/2008 | Feldon et al. |
| 2008/0259274 | A1 | 10/2008 | Chinnock |

OTHER PUBLICATIONS

P.J.Saine, "Focusing the Fundus Camera: A Clinical Approach," Journal of Opthalmic Photography, vol. 14, No. 1, pp. 7-24, Sep. 1992, Madison WI, US. EFS file name: 20130430_13-512336_IDS_NPL_Cite2.

M.A.Mainster et al., "A Wide-Field, High-Resolution Opthalmoscopic Contact Lens," Opthalmic Surgery, Lasers & Imaging, Jan./Feb. 2003, vol. 34, No. 1, pp. 76-77, US. EFS file name: 20130430_13-512336_IDS_NPL_Cite3.

C.Gliss et al., "Toward a miniaturized fundus camera," Journal of Biomedical Optics, 9(1), 126-131 (Jan./Feb. 2004). EFS file name: 20130430_13-512336_IDS_NPL_Cite4.

E.Dehoog et al., "Optimal parameters for retinal illumination and imaging in fundus cameras," Applied Optics, vol. 47, No. 36, pp. 6769-6777, Dec. 20, 2008, US. EFS file name: 20130430_13-512336_IDS_NPL_Cite5.

Ye et al., Chinese Optics Letters, Optical configuration of fundus camera based on inner focusing manner, vol. 8, No. 7, pp. 689-692, Jul. 10, 2010, CN. EFS file name: 20130430_13-512336_IDS_NPL_Cite6.

PORTABLE FUNDUS CAMERA

CROSS-REFERENCE TO RELATED PATENT APPLICATIONS

This application claims priority from U.S. provisional patent Application No. 61/266,564 filed Dec. 4, 2009, the disclosure of which is incorporated herein by reference.

STATEMENT REGARDING FEDERALLY SPONSORED RESEARCH OR DEVELOPMENT

This invention was made with United States Government support. The U.S. Government has a paid-up license in this invention and the right under limited circumstances to require the patent owner to license others on reasonable terms as provided for by the terms of Grant No. 1R43EY020714-01 awarded by the National Institutes of Health.

TECHNICAL FIELD

This invention relates generally to imaging the back of the eye, and more particularly to a fundus camera for such imaging.

BACKGROUND ART

Vision is one of the most valued of human sensory experiences. Vision loss is an often feared untoward health event associated with serious medical, psychological, social, and financial consequences. The preservation of vision has thus been an important goal of health interventions and is recognized as such by the World Health Organization, the United States Congress, and the U.S. Centers for Disease Control. As reported in the Vision Preservation Act of 2008 in the United States Senate:
  An estimated 80 million Americans have a potentially blinding eye disease;
  19.1 million Americans report trouble seeing;
  One million Americans are legally blind;
  The number of Americans who are blind or visually impaired is expected to double by 2030;
  It is estimated that blindness and visual impairment cost the Federal Government more than $4 billion annually in benefits and lost taxable income, and cost the United States economy approximately $51.4 billion annually in direct medical costs, direct nonmedical costs, and indirect costs such as lost productivity and wages;
  Recognizing that the [United States government advocates] a public health approach to visual impairment, the Department of Health and Human Services dedicated a portion of its Healthy People 2010 initiative to vision. The initiative set out as a goal the improvement of . . . visual health through prevention, early detection, treatment, and rehabilitation.

More specifically, vision loss can be caused by many factors, stemming from damage to all parts of the visual system. Retinal and optic nerve problems have emerged as leading causes of visual loss in developed countries. These posterior segment ophthalmic conditions are major and growing causes of vision loss globally, as well. Fortunately, many of these conditions, such as neovascular age-related macular degeneration, diabetic macular edema, proliferative diabetic retinopathy, retinal detachment, and glaucoma are treatable. In most of these cases, early diagnosis and proper follow up leads to adequate maintenance of visual function for life. Visualization of the retina and optic nerve by expert clinical readers is currently required to identify these pathologic changes, and the timely initiation of interventions for these back of the eye conditions is paramount to preserving vision. Furthermore, the early diagnosis of conditions such as dry age-related macular degeneration can help patients address risk factors for progression and thereby delay and possibly prevent long term visual loss. Generally, a retinal examination is performed by a trained clinician. The findings of the examination are then optimally documented through fundus photography.

There are number of various fundus cameras that are currently available on the market. For a summary of such cameras, one may refer to E. DeHoog and J. Schwiegerling, "Fundus camera systems: a comparative analysis," *Appl. Opt.*, 48, p. 221-228 (2009). For a summary of certain fundus cameras disclosed in the patent literature, one may refer to U.S. Patent Application Publication US 2008/0231803, "Compact Ocular Fundus Camera" of Feldon et al., the disclosure of which is incorporated herein by reference.

Bulky, expensive table-top fundus cameras are typically used to acquire high quality true-color and angiographic images of the retina with large fields of view. The operation of these table-top cameras is very elaborate, and requires a highly trained technician. A number of hand-held fundus cameras have also been developed in the past, including a contact type camera, the RetCam, sold by Clarity Medical Systems Inc. of Pleasanton, Calif., which is mainly used for infant ophthalmoscopy. These cameras, while having a smaller form-factor than the table-top devices, still lack the simplicity and portability of a device amenable to widespread distribution. The hand-held units in these cameras are bulky and are attached to a base-station via a thick cable. Alignment and focusing of the cameras is not intuitive, and in some versions the size of the field of view is inadequate. In addition, these cameras do not provide a significant reduction in cost, while lacking the imaging quality of the table-top cameras.

At this time, fundus photographic systems are typically available only in high-end, high-overhead technology dominated ophthalmic and optometric medical practices. Not all patients who could benefit from retinal fundus photography have access to it, even if they have a primary eye care provider. Likewise, those patients that rely on general practitioners, family practice physicians, internists, and pediatricians for ophthalmic health concerns have essentially no access to comprehensive retinal imaging. Moreover, special populations, including residents of nursing homes, assisted living facilities or group homes, prisoners, remote populations such as Native Americans on reservations and people residing in very rural communities have restricted access to a comprehensive and well documented fundus evaluation, and fundus imaging. The problem is even more severe in developing nations, and also in many Western countries where expensive heath care technology is more controlled, such as by government mandate.

It is further noted that rates of visual loss increase with age. Not surprisingly, ophthalmic screening programs have become increasingly important as the population ages in the United States and around the world. It was estimated by National Health Interview Survey (NHIS) that 9 million Americans 45 to 64 years of age had vision loss in 2006. As U.S. "baby boomers" age, the number of seniors at risk for vision loss will continue to grow. It has been documented that vision loss in this population results in decreased quality of life, increased healthcare costs, and increased risks of household accidents, including falls. Visual loss increases rapidly with age; over 25% of people are affected after age 74. Additionally, the American Academy of Ophthalmology recommends that people 65 or older should have a comprehensive eye examination every 1-2 years. Treatment, management, and prevention can effectively change the course of various conditions that result in visual loss, and oftentimes avoid blindness. Despite the proven benefits of ophthalmic evaluation, fewer than 10% of non-ophthalmologists or non-optometrists can effectively examine an eye using a direct ophthalmoscope. In addition, the direct ophthalmoscope has a very high magnification and small field of view, so that identifying disease processes may be problematic even to the trained practitioner. Furthermore, the traditional ophthalmoscope does not provide a way to record images, and thus, it is not possible to perform accurate follow up of disease progression over a period of time.

Glaucoma is treatable and can be diagnosed by identifying damage and signs of change of the optic nerve. Macular degeneration is treatable and can be identified by drusen, exudates, and hemorrhage in the macula. Diabetic retinopathy is treatable and can be diagnosed and followed by evaluating the optic disc, macula, and retinal vessels for multiple well described findings. Documenting changes over time in the eye is critical for proper diagnosis and treatment of all of these conditions.

Early detection and therapy of early eye diseases results in better vision for elderly patients. There has thus been increasing emphasis on ophthalmic imaging technologies as standards of care. Existing fundus cameras are expensive (e.g., $20,000 to $45,000 or more), require considerable technical expertise to operate, and are not easily portable. As a result, fundus photography as a screening tool has been implemented only to a very limited extent. The widespread implementation of fundus photography and usage in remote areas has so far not been practical. A low magnification, large field of view, user friendly, portable, cheap, and durable, fundus camera would be extremely beneficial in helping reduce rates of blindness. The benefits of a new method of photographic documentation of a patient's retina would be cost effectively expanded to large populations, thereby allowing for expert diagnosis, appropriate follow up, and optimal management to reach at-risk patients in all areas of our nation and the world.

In summary, there is therefore a need for a hand-held, durable, portable, and easy-to-use digital fundus low-cost camera, which can significantly improve patients' access to the high quality fundus images required to manage retinal and optic nerve diseases. The portability and versatility of such a device would enable the implementation of retinal imaging in large populations that previously did not have easy access to such technology.

DISCLOSURE OF THE INVENTION

The present invention meets this need by providing a compact portable fundus camera device. The camera can be used by individuals of varying backgrounds. For example, a retina specialist might utilize one such device in each exam lane to speed patient flow; optometrists or general ophthalmologists might find the device economically most favorable as the only mode of photographic documentation of the fundus in their practices; and a primary care provider might use it to document and follow childhood diabetics and patients with other conditions that affect the eyes. The camera enables a user to obtain one or more digital images of the fundus of a patient, deliver such images electronically to an expert reader of such images, and consult with the expert for advice as needed. Health aides, technicians, or nurses may be trained to use the camera to obtain retinal photographs of underserved populations.

In these settings, the images may be stored and digitally transmitted to qualified image readers to determine the need for further patient observation and/or referral to other medical specialists. The camera is compatible with hand held computing and image viewing platforms such as an iPhone®, or Android™ phone, and can be easily integrated into the growing and dynamic field of remote health monitoring. In so doing, the Applicants' camera can play an important role in helping improve the quality of medical outreach programs as well as reduce rates of blindness and visual disability worldwide.

Additionally, the Applicants' camera particularly benefits a growing segment of our populace, the aging population. The instant camera device has utility for population based screening for potentially blinding retinal and optic nerve diseases, with the potential for significant health and direct and indirect medical cost savings in the geriatric population.

In accordance with the present invention, there are provided modifications and improvements in imaging the fundus, using the Applicants' camera system, which is portable. In certain embodiments, aspects of the invention include lenses, methods of focusing, illumination systems, lens configurations, and compatibility with hand held computing and/or imaging platforms. In another aspect, the use of image stitching software for mosaic image creation is described. In another aspect, reusable or disposable covers are described for antisepsis and protection of the innovative camera described herein.

More specifically, in accordance with the invention, there is provided a camera for imaging the fundus of an eye, the camera comprising a housing comprising an internal cavity terminating at a forward housing end, a forward lens, and a light source configured to direct light from locations distributed around the perimeter of the forward lens forwardly out of the housing end. The camera may be further comprised of a protective cover removably joined to the forward housing end and in contact with the forward lens. The cover may be comprised of a central lens in contact with the forward lens. The forward lens may have an exterior surface having a curvature to render it contiguously contactable with the cornea of the eye. The forward lens may be suspended in the housing on a cushioning mount and may be rearwardly displaceable by contact with the eye. The camera may include a sensor that detects pressure of the forward lens against the eye.

In accordance with the invention, there is also provided a camera for imaging the fundus of an eye, comprising optics configured to focus light reflected back from the fundus onto an image receptor, with the optics being capable of varying the field of view among differing portions of the fundus. In certain embodiments, the optics are aligned along an axis, and may be comprised of a prism rotatable around the axis to vary the field of view among differing portions of the fundus. In other embodiments, the optics may be comprised of a first and second reflective elements arranged in a Cassegrain configuration to vary the field of view among differing portions of the fundus. In other embodiments, the optics may be contained in a swivel fixture to vary the field of view among differing portions of the fundus. The camera may be further comprised of an image processor containing an algorithm for stitching images from different fields of view of the fundus to form a composite image of the fundus.

In accordance with the invention, there is also provided a method of imaging the fundus of an eye comprising contacting a hand-held camera with the cornea of the eye; directing light from locations distributed around the perimeter of a forward lens of the camera forwardly out of a housing end of the camera through the pupil of the eye and onto the fundus; receiving light reflected back from the fundus onto an image receptor in the camera; and processing data from the image receptor to create a digital image of the fundus. The method may be further comprised of forming the digital image by stitching together separate images of different portions of the fundus.

Ultrasound probe technology is also disclosed herein, with particular regard to portable computing platforms. In one embodiment, an ultrasound/B-scan device may be connected to a portable computing platform. Uses of such a device include ophthalmic, abdominal, and obstetric. In a related aspect of the invention, improvements are provided in many types of medical imaging and diagnostic technologies, including the miniaturization and integration of advanced medical diagnostics technologies with hand held computing and imaging platforms. A specific problem related to retinal fundus photography is evaluating the posterior segment of the eye when there is a media opacity. Such evaluation often requires bulky, expensive, and complicated B scan ultrasound device systems. Currently a large expensive system is needed to evaluate the eye in these cases. A personal computer interface is often required, as well.

Thus, also disclosed in this invention is the utilization of iPhone®, Android™, or similar hand held imaging and communication device technology platforms with a battery powered, hand-held ultrasound probe. The probe can communicate to the personal digital assistant, iPhone®, or Android™ system via wireless communication (e.g. Bluetooth®) or a cable, and the ultrasound image can be viewed in real time in a portable manner. The ultrasonic images can be saved directly on the hand held imaging platform, or on software embedded in the probe itself. Ophthalmic axial length measurement may also be performed with this device.

These ophthalmic applications fill an unmet need, because in developing countries and remote locations, access to ultrasound imaging can be necessary but difficult or not possible. This adaptation of the technology will improve patient care in many scenarios. The ultrasound imaging system is not limited to ophthalmic use but can apply to obstetric, emergency, abdominal, carotid, vascular, and other soft tissue and orthopedic ultrasound technologies.

Furthermore, in accordance with this invention, other ophthalmic and medical imaging systems such as corneal topography, tomography, keratometry, pupillometry, aberrometry, pachymetry, and autorefraction can be miniaturized to a hand held device that interfaces with a hand held portable computing platform, such as an iPhone® or Android. The integration of these technologies with hand held computing systems will allow for safer patient care (e.g., direct integration with electronic digital files), less loss of data, and ease of use for technicians, physicians and other examiners. In all cases, the direct diagnostic modality is converted to a portable and hand held system compatible with iPhone®, Android™, and similar platforms. Software applications can be downloaded into the device to manage the image display, identification and storage processes. Additionally, for all systems, analysis software to aid in automatic interpretation and diagnosis can be integrated into the computing platforms.

Another problem addressed in this invention is patient name and data tracking. It is, of course, critical, that any diagnostic study, whether it be fundus photography, ultrasonography, or other, that the study is properly matched with patient name and a unique storage/file identification number. One solution to this problem is based on data review and/or entry. For example, the portable fundus camera or ultrasound device may have a numerical display or entry system, which establishes a reference to a patient name stored elsewhere. The device could generate a numerical code for each image, with the device user recording the number on a patient's medical record or in the hand held portable computing device such as the iPhone® or Android™ for data management, and also to clearly identify which eye is being studied. Alternatively, the device user may enter the patient's medical record number into the device, along with indication that the right or left eye is being studied, with the device storing this information for download later. Alternatively, the image may be saved on a personal computer or other computer at the time it displayed on the portable imaging system, with the patient's name. However this method has the risk of confusion and data loss if the file save is not made at the exact moment a patient is examined.

There is therefore a need for a better and more precise tracking system. Thus an additional aspect of the invention is the use of data tracking systems to facilitate this identification and data tracking process. In one embodiment, the use of radio frequency identification (RFID) tags for patient and eye identification may be coupled with a hand held fundus camera or other portable diagnostic imaging technology integrated into a hand held computing/imaging system. For example, a unique RFID tag (either a single RFID that resonates with a set unique frequency, or a combination of several RFID tags together), or other methods for creating a unique value known to those skilled in the art can be placed in a sticker, or an adhesive backed substrate. The "RFID sticker" will be unique for each subject and eye, and could be included with the instrument's packaging, or distributed separately. When beginning use on a patient, the camera, ultrasound, or other diagnostic device will ask for the RFID information, and then read the RFID and use that number to assign the image a unique identifier. For fundus imaging or other eye observations or measurements, there may be two unique ID numbers for each patient that could be utilized, i.e., one for each eye. Alternatively, there could be one unique number, with the camera or imaging device prompting the user to enter the right or left eye as being examined. The sticker may have the code written in ink on its surface, which may be tracked by placing it on the patient's chart and/or placing the sticker in a log book where every study is captured and matched with a unique code.

Bar code technology may also be utilized in a similar way, as could a small hand held scanner that records a patient name, and then emits a wireless signal that is captured by hand held computing system and/or camera as they interface together to generate a tracking number. It may be desirable to separate out the RFID, scanner, and/or reader into a separate device to accomplish the unique tracking identification process, or in some versions of the invention, the reader may be integrated into the camera. Thus, an aspect of this invention is to use the portable fundus camera, or other applicable diagnostic imaging or medical hand held diagnostic technology with systems that can facilitate electronic unique patient information tracking. An example of RFID products and applications that may be adapted in to the hand held fundus camera is as disclosed by the Texas Instruments Incorporated at the Internet web page URL http://www.ti.com/rfid/shtml/apps-asset-tracking.shtml.

For the instant fundus camera, there may also be provided a hand held device where the name or medical record number is entered either mechanically or digitally, and the camera then takes a photograph of that name, or image of the name. In use, each captured retinal image would be required to have a predicate unique identifier subject name photographed, with the images are downloaded in pairs, i.e., name and photograph. Such a method ensures that a photograph is always associated with the patient's name. The camera may further include an attachment that enables a medical record and name to be imaged from paper, or it may require a special optical instrument adapted to the camera such that the name is entered into the device and then the camera is attached and the photograph is made.

A simple scanner with or without character recognition technology could also be integrated into the system, such as a modified business card reader that captures name and birth date and matches it to a unique file on the retina camera or other hand held device. Alternatively, a voice recognition system may be used where the user speaks the name and birth date and voice recognition systems digitize the file and code it to a unique photograph. The quick response (QR) code reader and generator systems, or similar data matrix technology, may serve as the fundus camera interface to ensure unique and accurate data tracking. Technology that may assist in automated or simplified matching of subject name and/or identifiers (i.e. date of birth, medical record number, site, age) with the image (or retinal photograph) is a further aspect of this invention, including RFID technology, QR code technology, bar code technology, scanners, and photographic interfaces associated with hand held cameras for image tracking. Alternatively, images taken by the device may be linked to the patient in a database using fundus recognition, in a manner similar to that used in fingerprint recognition. The camera may also have a small electronic peripheral that can serve to print out (possibly on a sticker) the unique identifier so it can be placed in a permanent (non-electronic) file for reference to subject name.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by this specification, drawings and claims.

BRIEF DESCRIPTION OF THE DRAWINGS

The present disclosure will be provided with reference to the following drawings, in which like numerals refer to like elements, and in which.

Figure 1A:
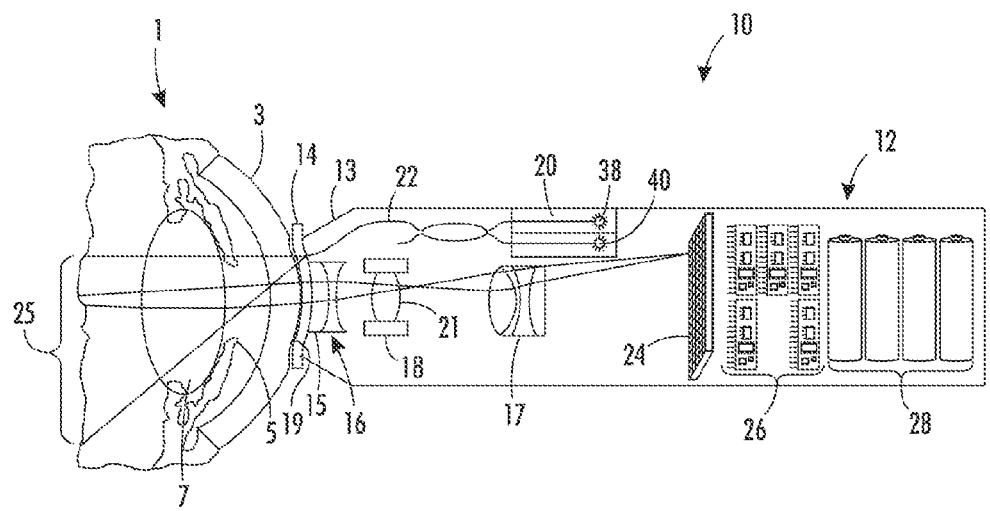
FIG. 1A is a schematic diagram of the fundus camera of the present invention.

The present invention will be described in connection with a preferred embodiment. However, it is to be understood that there is no intent to limit the invention to the embodiment described. On the contrary, the intent is to cover all alternatives, modifications, and equivalents as may be included within the spirit and scope of the invention as defined by the appended claims.

BEST MODE FOR CARRYING OUT THE INVENTION

For a general understanding of the present invention, reference is made to the drawings. In the drawings, like reference numerals have been used throughout to designate identical elements. The description provided herein may identify certain components with adjectives such as "top," "upper," "bottom," "lower," "left," "right," etc. These adjectives are provided in the context of the orientation of the drawings, which is arbitrary. The description is not to be construed as limiting the instant fundus camera to use in a particular spatial orientation. The camera may be used in orientations other than those shown and described herein.

In describing the present invention, a variety of terms are used in the description. As used herein, the term "fundus" is used with reference to the eye, and is meant to indicate the interior surface of the eye, opposite the lens, including the retina, optic disc, macula and fovea, and posterior pole.

Overview

The retinal imaging system of the instant fundus camera utilizes multiple features in its optical design and function to provide a compact, hand-held, user-friendly camera that is capable of acquiring retinal images with sufficient quality for a physician or trained ophthalmic technician to conduct a quick and satisfactory fundus examination. The data output of the camera, comprising a uniquely identified mosaic image, is compatible with storage and display on novel handheld computing platforms as well as more traditional computer systems. The software platform of the camera is compatible with medical telemetry and electronic medical records systems. The camera device is useful in many medical settings, including uses in ophthalmic, optometric, internal medicine, pediatric and general practice offices, nursing homes, chronic care facilities, prisons, and regions of the world where there is need for better access to ophthalmic and medical care. Its use simplifies human retinal inspection and image capture during routine patient visits and increases the availability of the very important ophthalmic diagnostic intervention of fundus photography.

When in use on a patient, the instant fundus camera contacts the cornea, with confirmation of optimal alignment therewith. Once aligned, the image of the fundus is may then be displayed on a handheld computing platform or hand held imaging device such as an iPhone®, Android™, or on a laptop or personal computer. The data is also stored in the camera for later examination by a trained reviewer.

1. General Configuration

FIG. 1A is a schematic diagram of the fundus camera of the present invention, which illustrates the general principles thereof. The camera 10 may be operated as a hand-held instrument, comprising a housing 12 that may be shaped as a cylinder or any other form that is convenient for easy manipulation. The camera 10 is further comprised of an eye contact membrane 14, imaging optics 16, a focusing mechanism 18, a light source 20, optical fiber 22, a charge coupled device (CCD) 24, image processing electronics 26, and a power supply 28. It is to be understood that in FIG. 1A, the components of the camera 10 are illustrated schematically, and may not be to scale.

Figure 1B:
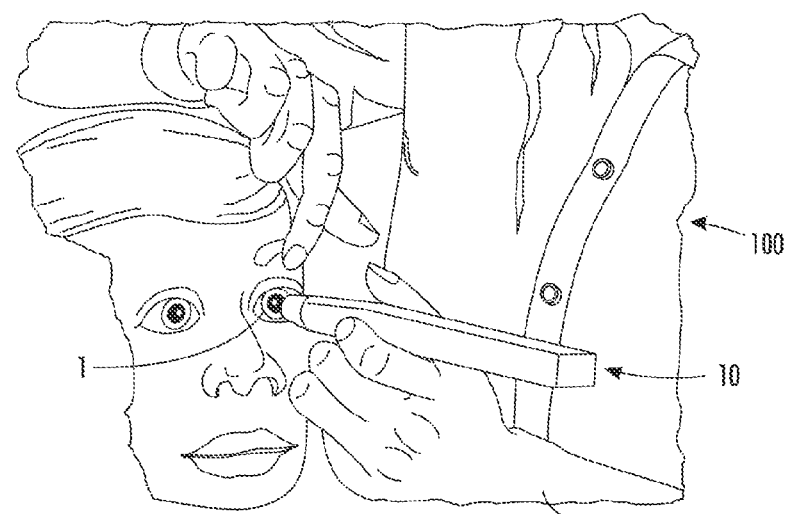
FIG. 1B is an illustration of the fundus camera being used to image the eye of a patient.

Referring also to FIG. 1B, in using the camera 10, a health care provider or technician 100 holds the camera 10 in one hand 102 and brings it into the contact with the anesthetized cornea 3 of a patient's eye 1. Once in the contact with the cornea 3, the camera 10 performs internal calibration and initialization steps and communicates with the operator 100 to initiate capture of a high quality image. Upon achieving best focus, the camera 10 digitally records an image or multiple images of the fundus using sufficient illumination, which may be provided by the camera as will be explained subsequently herein. The images are analyzed for completeness with regard to target field of view requirements, and a signal is sounded when the image quality is deemed to be acceptable by the camera's electronics 26 and software. The time duration between the contact with the cornea 3 and the image acquisition may be less than about five seconds, which facilitates ease of use and broad applicability.

After the image acquisition is complete, the image may be transmitted wirelessly (e.g., via a "Bluetooth®" communication) or transmitted through a connector cable (not shown) to a nearby personal computer (not shown) or a hand-held computer, such as an iPhone®, Android, or other hand held imaging system (not shown) for viewing and storage. Additionally, a copy of the image may be stored in the on-board memory of the camera 10, so that it can later be transferred to a computer via a USB or other fast connection.

The imaging optics 16, light sources 20 and processing electronics 26 may be integrated inside the housing 12. The front of the housing 12 contains a lens 15 designed to oppose the cornea 3 during the imaging. To prevent damage to the cornea 3 and to prevent the spread of infection between patients, a disposable or reusable lubricated thin plastic membrane or attachment 14 is used to cover the front lens 15. The lens 15 is shaped to fit the corneal curvature for most patients, and the lubricant in the attachment or cover 14 acts as a coupling agent and will enhance fit for cases when the curvature of the lens 15 is not perfectly matched with the curvature of the cornea 3. The lens or attachment that rests on the cornea may have a spring, cushion, or other protective mechanism (not shown) to reduce the chance of putting excess pressure on the eye. The cover 14 may be treatable with antiseptic. The front lens 15 or the contact portion 19 of the membrane or cover 14 may contain a prismatic component (not shown) to enable mosaic image acquisition through a smaller single image field of view, thereby allowing for reductions in illumination requirements.

In one embodiment, the cover 14 is formed with the central region functioning as a lens. The lens may serve to direct light supplied by the camera 10 to the fundus with the desired distribution, and/or it may also serve as a lens working with other internal optics of the camera 10 to focus light reflected back from the fundus onto the CCD 24.

The light that is needed to illuminate the fundus for imaging is delivered to the cornea-lens interface via multiple optical fibers 22 (see also FIG. 4A) embedded in the front eye-contacting lens assembly of the camera 10. The illumination light enters the eye 1 through an annulus at the periphery of the dilated pupil 5, while the imaging is relayed through the central portion of the pupil 5. Such an approach helps to avoid image deterioration due to reflections and scatter off the surfaces and volumes of the cornea 3 and crystalline lens 7. The light cone directed into the eye from the front assembly of the camera is configured to minimize lenticular scatter. The illuminated retina 2 is imaged by the camera optics 15 and 17 onto a CCD array 24. Upon initial patient contact, only invisible infrared (IR) light is used to illuminate the retina. The IR illumination (or a low light capture system) is used by the camera 10 to analyze the alignment and stability of the camera 10, and to adjust the focusing mechanism 18 to achieve sharp imaging. When the alignment steps are completed, visible light is used to acquire high quality color images that can be integrated with software to create a mosaic image.

After use, the disposable cover 14 is removed, the front lens 15 is cleaned and a new protective cover 14 can be fitted for the next patient or as a temporary protector, allowing for pocket storage of the camera during clinical use. The camera device 10 may be inserted into a protective container (not shown) for storage. The durable light weight and compact configuration of the camera 10 enables and facilitates simple use in a medical practice. While the clinician or ophthalmic technician is moving in the exam lanes or office area, the camera can wirelessly connect with the main server of the office and synchronize the acquired images, which are then extracted for detailed analysis.

The camera 10 may have a very simple user input interface. It may have a ready button (not shown), which puts the camera 10 into a prepared state for acquisition of a new image. In addition, it may have a simple LCD screen (not shown) and numeric input buttons (not shown) that are used to identify the patient to the camera 10 using a unique identifier number. As previously mentioned, there are several methods (such as photographing a written identifier, utilizing bar code or RFID technology, etc.) for tracking and identifying unique patient images captured by the camera 10. The LCD screen may also be used display a quality metric of the acquired image, based on the results of the analysis. For example, a scale of 1 to 10 may be used, with 1 as the least acceptable image quality score and 10 as the best image quality score. It may be left up to the specific need of the physician or other medical authority to establish preferences for image acceptability, for example, by instructing a technician to accept images with the quality score of 5 and above, while rejecting the images with lower score. In that manner, acceptable image screening can be carried out. The LCD display may also contains an indicator showing the amount of the remaining battery charge, the number of acquired images contained in memory, the remaining memory capacity, and other relevant information. At the end of a working session, the camera 10 may be placed into a charging cradle (not shown), or connected to a USB port of a PC for charging of the batteries 28 contained therein.

2. Imaging Optical Design

Figure 2:
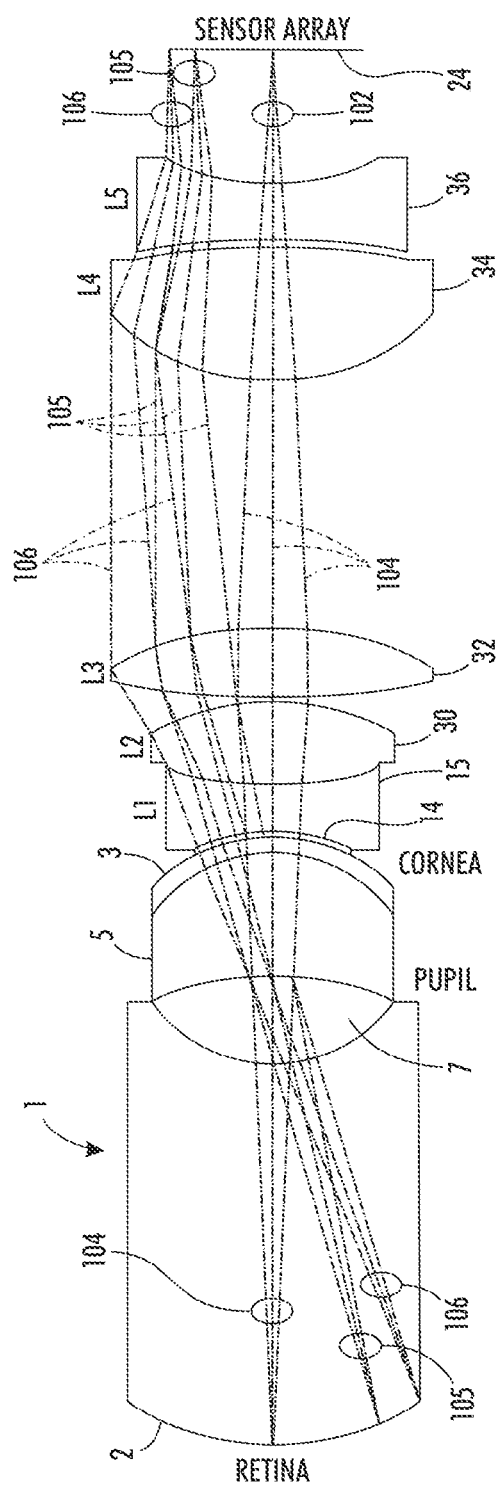
FIG. 2 depicts an optical configuration of the camera imaging the eye of a patient.

FIG. 2 depicts the optical configuration of the fundus camera 10 imaging the eye 1 of a patient. For the sake of simplicity of illustration, only a portion of the eye is shown. The left-most surface 2 represents the retina, and the right-most surface 24 designates the imaging array or charge coupled device. The design and ray simulation was conducted using ZEMAX® optical design software produced and sold by the Zemax Development Corporation of Bellevue, Wash.

In this basic description of the camera 10, the eye 1 is treated as a perfect optical instrument. The rays that originate at the retina 2 and represent the reflected light are perfectly collimated when exiting the corneal surface 3. The retina 2 of the model eye 1 is represented by a flat surface, and the focusing power of the eye is modeled using an ideal thin lens at the location of the pupil 5. The cornea surface 3 in this particular model does not possess refractive power and is represented by an imaginary surface in air with a nominal spherical radius of curvature of 7.8 millimeters (mm). In this embodiment of the fundus camera 10, the diameter of the contact area of the front lens 15 with the cornea 3 is 5.8 mm, while the size of the dilated pupil 5 is 7 to 8 mm. The surface of the cornea not covered by the lens 15 is used for passing light from the fiber optics 22 therethrough to illuminate the retina 2. Overall system length, from the contacting lens 15 to the sensor array is 30 mm. With changes in lens size and power, this length may be reduced.

In an actual human eye, the biological tissue thereof does not posses ideal optical characteristics, and thus the refractive properties of the crystalline lens 7 and the cornea 3 are not perfect. The lens 7 has a refractive index gradient as part of its refractive properties, while the surface of the cornea 7 deviates in its shape from a sphere for all people. As the result, optical surfaces within the eye 1 create aberrations in the image of the retina 2. Accordingly, a more realistic schematic eye model may be used to design the imaging system of the camera 10.

The elaborate optical design is used to partially compensate the aberrations of the lens 7 and the cornea 2 in the standard free-space ophthalmoscopes. In the present case, the final optical design may be somewhat simplified due to the contact of the lens 15 of the camera 10 with the cornea 3, thereby eliminating the air-corneal interface, and slightly conforming the corneal surface as shown in FIG. 1A, thus removing corneal aberrations. In addition, the contacting lens 15 effectively eliminates the refractive power of the cornea 3, and thus allows the optical designer to choose the appropriate f/# of the optical system to image the retina 2 through the pupil 5.

Referring again to FIG. 1A, a disposable transparent insert 14 covers the front of the contact lens 15. The thickness of the insert 14 is approximately 100 microns, and it is used to ensure antisepsis with a new sterile contact system for each patient, protect the cornea 3 from the hard glass material of the front lens 15, and to protect the front lens 15 of the camera 10 from scratches. The insert 14 may be disposed of and replaced by a fresh one after each use on a patient. The insert 14 may be made of 2-hydroxyethyl methacrylate (HEMA), polyvinylidene chloride, polyethylene films, or of another suitable biocompatible polymer. It is noted that the polymer need only have short time biocompatibility, as the corneal touch time will be very short. Both sides of the insert 14 may be coated with hydroxypropyl cellulose (sold commercially as Goniosol™ 2.5%, and under other brand names.). The presence of the liquid between the contacting lens 15, the insert 14, and the eye 1, in addition to improving comfort to the patient, allows for the filling of potential gaps that exist due to the shape deviations of the actual cornea 3 from the curvature of the contacting lens 15, thereby reducing optical aberrations when the camera 10 is capturing images of the fundus.

The optical system of the camera 10 is designed for 40 degrees of full field of view (FOV), which is comparable to most of the commercial table-top fundus camera instruments currently available on the market. Referring again to FIG. 2, the full field of view is illustrated by the fans of rays 104, 105, and 106 originating at the retinal surface 2. in the imaging of a typical eye 1, such a FOV corresponds to a ring of approximately 12.5 mm in diameter. Referring to FIG. 3B, a fundus image obtained from the camera 10 may in final form be a mosaic of separate images. The fundus image 110 is a mosaic or composite image of five separate images 110A-110E. The combining of the images 110A-110E may be done through the use of image stitching software. The image stitching software can stitch multiple (more than five total) images together to account for overlap and poor quality. The software system may in some embodiment choose the highest quality aspects of each image for optimal end image quality. By using the capability to "stitch" (combine) a set of images together to obtain a complete fundus image, the size requirement for an individual image obtained by the camera 10 is reduced. This enables mechanical aspects of the camera device 10 to be simplified, since smaller images mean smaller field of view, which greatly reduces the complexity of the optical design. For example, a direct ophthalmoscope has very simple optics but a very small field of view.

Figure 3A:
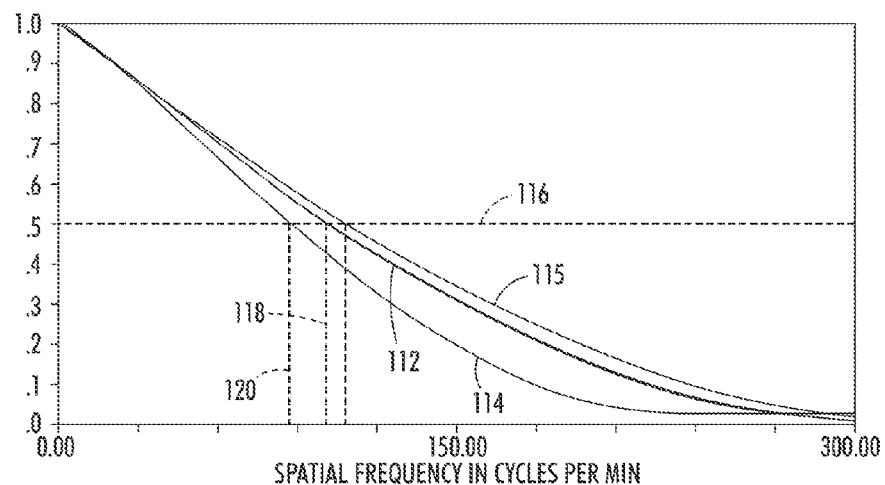
FIG. 3A depicts the modulation transfer function of one embodiment of the fundus camera.
Figure 3B:
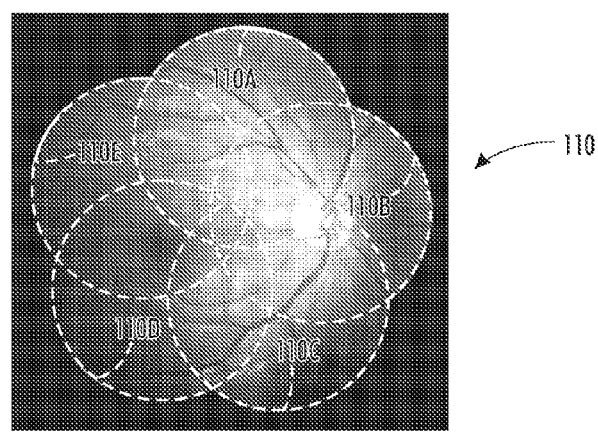
FIG. 3B depicts the utilization of mosaic image stitching to combine five separate images of portions of a fundus, thereby producing a single high-resolution image of a fundus.

FIG. 3A shows the polychromatic modulation transfer function (MTF) of the exemplary optical design of FIG. 2. The data for on-axis imaging is indicated by curve 112, and the data for the tangential and sagittal responses at the full-field periphery are indicated by curves 114 and 115 respectively. Assuming that the system resolution is defined at 50% of MTF (horizontal dotted line 116), the on-axis resolution 118 is 9.8 microns and the resolution 120 on the periphery of the field of view is 11.5 microns. The obtained resolution levels exceed the guidance provided by the International Organization for Standardization (ISO) standard 10940:2009 for fundus cameras, which lists 12.5 microns as the minimum resolution at the center of FOV, and 40 microns in the periphery.

The overall magnification of the imaging system is 0.7, which allows for imaging the retinal field onto a ⅓ inch CCD, which is a typical size having a sensing area of about 4.8 mm×3.6 mm. Provided that the size of a macular cone cell in an eye 1 is about 2 microns, the pixel size of the sensor array is 1.4 microns and the maximum number of pixels needed for imaging is 18 million. However, assuming that the pixel size is defined by the diffraction limit of 8.5 microns, the minimum required number of pixels is one million. Thus a CCD 24 with two to four millions pixels provides adequate sampling for obtaining good quality images of the fundus.

Referring again to FIG. 2, the focusing of the imaging system is accomplished by changing the distances between lenses 30 and 32 (L2-L3) and between lenses 34 and 36 (L3-L4). In this embodiment, the design provides a correction factor between −15 and +15 diopters. A lesser range of the correction factor, for example, +2 to −4 diopters is also an acceptable design. The range of motion for the L2-L3 distance is 0.52 mm, while the range of motion for the L3-L4 gap is 11.4 mm. In other embodiments of the optical system, the correction factor may be increased to allow for fundus imaging of small children or infants, or decreased for device simplification.

At least two different mechanisms may be implemented for focusing. In one approach, the focusing is accomplished by a mechanical translation, such as by using a piezo-based motor. One such linear motor is the SQUIGGLE® motor, manufactured by New Scale Technologies, Inc. of Victor N.Y. This motor uses piezo-materials to deform the motor body in an orbital processing fashion, thus translating a threaded shaft.

Such motors are described in U.S. Pat. Nos. 6,940,209, and 7,786,648, the disclosures of which are incorporated herein by reference.

The threaded shaft and motor body of a first piezo motor (not shown) may be operatively connected to respective fixtures (not shown) which hold the lenses 30 and 32, thereby enabling relative motion between them when the motor is operated. In like manner, a second piezo motor (not shown) may be operatively connected to respective fixtures (not shown) which hold the lenses 34 and 36, thereby enabling relative motion between them. In that manner, focusing capability of the camera 10 is provided. The main advantages of using such a motor include extreme miniaturization of the motor, high precision, speed, robustness, low to minimal noise, and smoothness of operation. Other mechanical or micro-machine systems including micro-electromechanical systems may also be suitable for the translational focus requirements.

Because the fundus camera 10 may be subjected to rough handling (e.g., accidentally during use, or during transportation), other focusing mechanisms are contemplated. In one embodiment, a liquid lens may be used as the focusing mechanism 18. Such liquid lenses are disclosed in e.g., "Adjustable fluidic lenses for ophthalmic corrections," R. Marks et al., *Opt. Lett.*, 34, p. 515-517 (2009) and in "Astigmatism and defocus wavefront correction via Zernike modes produced with fluidic lenses," R. Marks et al., *Appl. Opt.*, 48, p. 3580-3587 (2009). Additionally, such liquid lenses are manufactured by Varioptic SA of Lyon, FR. One may also refer to U.S. Patent Application Publication No. 20070002455 of Berge, and U.S. Pat. No. 7,245,440 of Peseux, RE 39,874 of Berge et al., U.S. Pat. No. 7,515,350 of Berge et al., and U.S. Pat. No. 7,602,557 of Berge et al., the disclosures of which are incorporated herein by reference.

Initially developed for use in mobile phones, a liquid lens is comprised of two unmixed liquids confined in a cell. The operation of the lens is based on electro-wetting, where the wetting properties of the cell, and thus the shape of the interface between liquids which translates to the focusing power, is affected by the applied voltage. As the result, the lens has a very fast response time; it can adjust the focusing power of the camera 10 within 50 msec. Such high speed is desirable in a fundus camera. Because of the cover 14 of the fundus camera 10 contacts the eye directly, contact time with the eye must be short to reduce the discomfort to the patient and maximize image acquisition. In one embodiment of a liquid lens provided by Varioptic, such lens is capable of 20 diopters of compensation power, has low power consumption (0.1 mW), is transparent to visible and near-IR light, is not affected by gravity or shaking, and has a large operating temperature range. Such a liquid lens may meet or exceed the performance of a translational focusing system. Other liquid lens systems may be suitable as means for focusing the camera 10, such as those that change power by silicone fluid forced in and out of a lens system, or piston-driven deformable lenses, where the central piston may push outward on a lens and alter the power of the lens.

3. Illumination Design

Figure 4A:
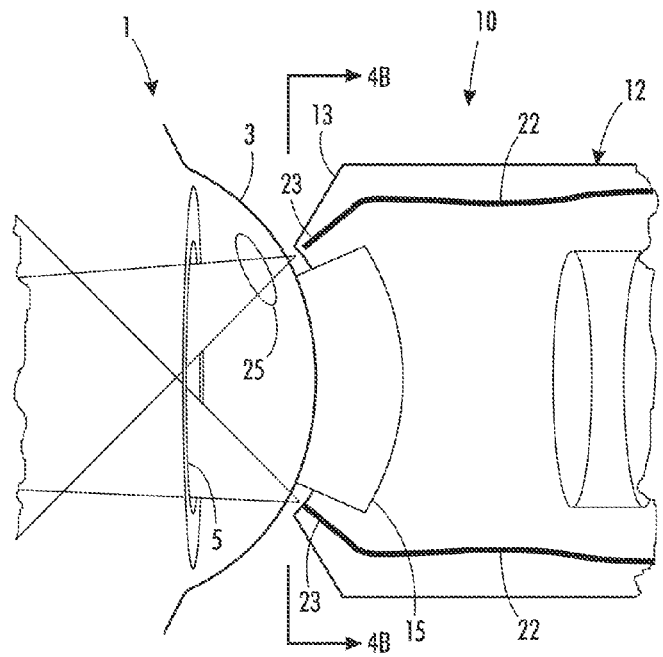
FIGS. 4A and 4B show the fundus camera head in cross section and plan view, respectively.
Figure 4B:
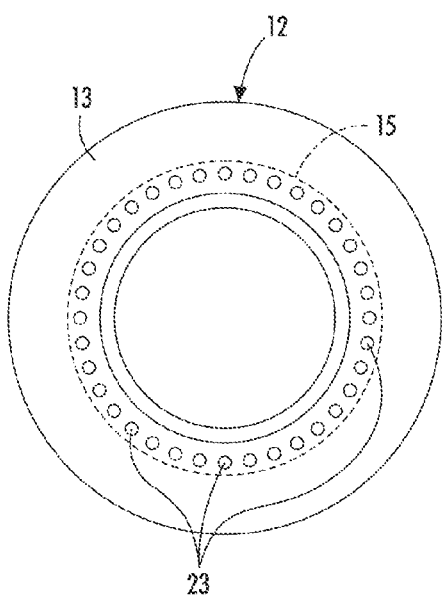

FIGS. 4A and 4B shows the fundus camera head (i.e., the eye contact end 13 of the camera) in cross section and plan view, respectively. In accordance with the Gullstrand principle, it is preferable that the path of the fundus illumination rays must be separated from the imaging path to prevent reflections off the cornea and crystalline lens from degrading the image. In the instant fundus camera design, the illumination is first directed into a bundle of optical fibers (not shown). The bundle is then split into individual fibers 22, which are terminated at their forward ends 23 near the front contact lens 15 of the camera 10. The fiber ends 23 are arranged in a substantially circular array around the front lens 15 and will be in close proximity to the cornea 3 during use. The size of a cone of light 25 emitted by a fiber end 23 is defined by the numerical aperture property (NA) of the fiber 22. Upon exiting a fiber end 23, an emitted cone 25 is not conditioned by any additional optics, but instead immediately enters the surface of the cornea 3. The NA of the fibers defines the fraction of the cornea 3 and anterior lens surface illuminated by each terminated fiber 22. The fiber NA is selected so as to prevent the light from the cones 25 from illuminating the parts of the cornea 3 and lens 7 (FIG. 1A) that are used for imaging paths. The NA of the fibers 22 also defines the size of the field of view of the retina 2 (FIG. 1A) illuminated in this configuration. The NA and number of illumination fibers may be adjusted to maximize image quality.

Figure 8:
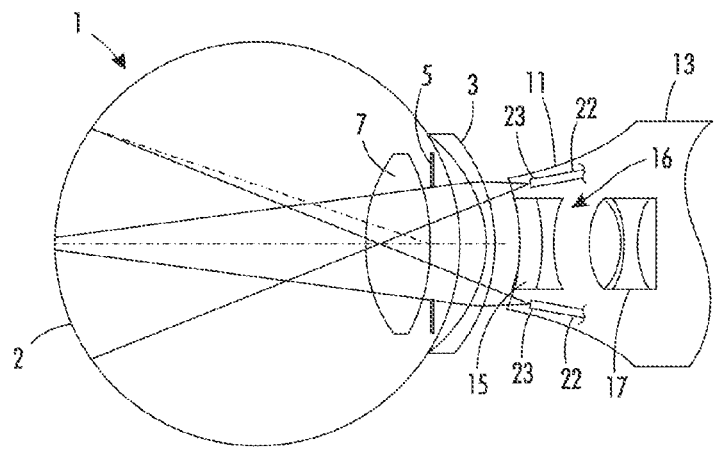
FIG. 8 is a cross-sectional schematic view of a first alternative fundus camera head.

Other configurations of the optical fibers at the forward end of the camera 10 may be suitable. FIG. 8 is a cross-sectional schematic view of a first alternative fundus camera head 13. It can be seen that the head 13 has a more tapered tip region 11, which facilitates the user seeing the placement of the camera on a patient's eye. The configuration of the optical fibers 22 around the lens 15 is substantially the same as depicted for the camera 10 of FIG. 4A.

Figure 9:
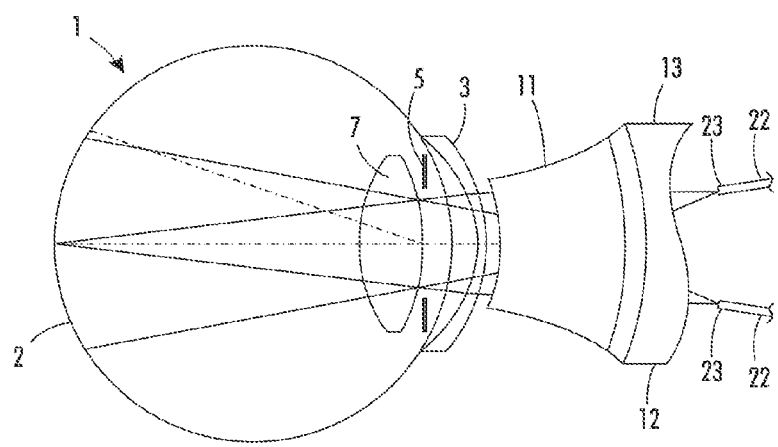
FIG. 9 is a schematic view of a second alternative fundus camera head.

FIG. 9 is a schematic view of a second alternative fundus camera head and lighting arrangement. In this embodiment, the illumination fibers 22 have been located further toward the posterior (non-contact) end of the camera 10. In this configuration, part of the imaging system (optics 16, which are concealed by the housing tip region 11) of the camera 10 is used to image the light provided by the circular fiber arrangement into the pupil plane. In essence, this is equivalent to placing the fiber ends 23 inside the eye 1, thus minimizing the size of the illumination beams as they propagate through the crystalline lens 7. In this case, the Gullstrand principle can be maintained for smaller pupil 5 and larger illumination cone, which is necessary for achieving the uniformity in the retinal illumination. Illumination vignetting is thus reduced.

Figure 5:
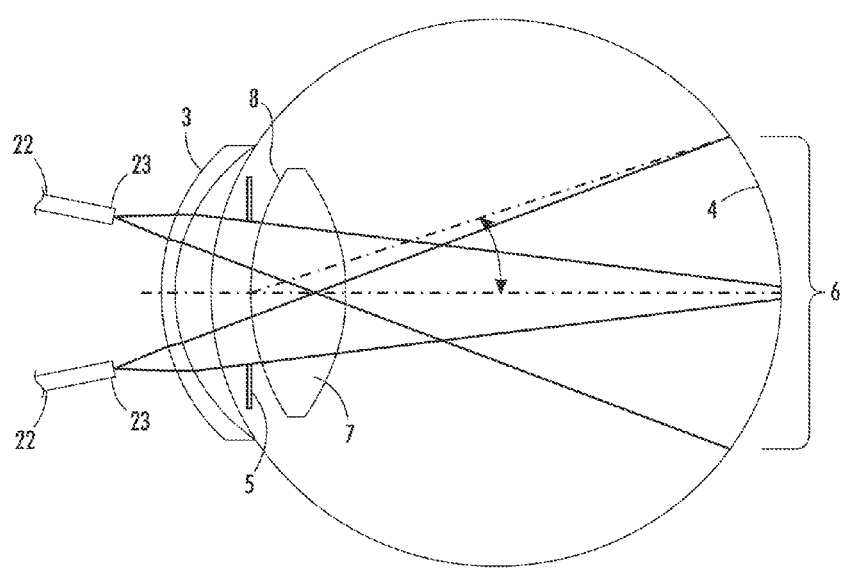
FIG. 5 shows an analysis of the illumination of a patient's eye with fiber optics.

FIG. 5 shows Zemax analysis of the illumination path for two NA=0.22 optical fibers, using an eye model, based on the tissue parameters listed in the publication "Wide-Angle Optical-Model Of The Eye," Pomerantzeff et al., *Am. J. Opt. Phys. Opt.*, 61, p. 166-176 (1984). It can be seen that the two oppositely located (upper and lower) fiber ends 23 illuminate the intended field of view 6 of the fundus 4, when the dilated pupil 5 is at least 6 mm. This approach follows the Gullstrand principle by separating the illumination rays from the imaging path in the cornea 3 and the anterior surface of the crystalline lens 7 through a 2 mm diameter portion of the pupil. Although the central part of the posterior half of the crystalline lens 7 is somewhat illuminated, the major contributing reflections off the surface of the cornea 3 and the anterior surface 8 of the lens 7 are eliminated in this approach.

Removal of the effects of the scattered light from the image results from the design of the illumination system of the instant fundus camera 10. In one embodiment, stray light that is scattered by the interfaces of the optical system and by the living tissue may be managed using stops, and/or by tilting and decentering of the optical components, and/or by configuring internal mechanical mounts and surfaces (not shown) to become baffles to absorb the stray light. Other methods to reduce light scattering are also contemplated. For example, some light may be scattered by the cornea 3 when it enters the eye 1. Such intra-corneal and intra-lens light scattering may interfere with quality of images obtained by the camera 10. Solutions to this problem include using filters, such as polarizing filters (not shown) or other optical systems (not shown) that allow light returning from only specific angles (i.e. angles consistent with retinal image formation on the CCD). Additionally, software algorithms may be used to remove scatter effects secondarily, particularly with image stitching technology. Furthermore, software may be used to grade the image quality, so that an image may be deleted or kept prior to observation and analysis of the image by an examiner. In a further embodiment, analysis software is provided with the camera, which can interpret certain types of pathology for the examiner in real time, or later, once the image is uploaded from the camera 10.

The use of multiple fiber-optics 22 enables the use of multiple light sources. Referring again to FIG. 1A, some of the fibers 22 may be coupled with an infrared light source 38, while others of the fibers 22 may be coupled with a visible flash light source 40. During the alignment mode, the camera 10 may illuminate the fundus 4 with infrared light. This is done to minimize the discomfort to the patient from bright visible light. Using the infrared illumination, the camera 10 performs auto-focusing steps by analyzing images acquired in real time. When the best focus is established, the IR light 38 is switched off, a visible light source 40 is switched on, which may be in the form of a flash, and a high quality image is acquired. Infrared light emitting diodes (IRLEDs) are suitable for IR illumination, because of their small size, low cost and low power consumption. The illumination requirements for IRLEDs are less stringent, because IR light is not used to acquire optimal images with high contrast. The exposure time and the number of IRLEDs can be easily modified to obtain sufficient quality video or real-time images sufficient for the image analysis algorithm to establish best focus position.

A flash or high output visible light source is preferred to acquire acceptable quality fundus images that have sufficient signal-to-noise ratio and that are free of blur due to the camera micro-movements. Several choices may be suitable: ultra bright LEDs, xenon light sources, or supercapacitor-based LED flash systems. The flash source should have sufficient luminosity to produce high contrast images in a camera having a high density CCD. In one embodiment, in which the camera 10 is comprised of a 5 megapixel CCD, the total energy incident on the CCD may be about $1.6 \times 10^{-7}$ Joules.

This number represents the amount of light scattered by the retina and collected thought the imaging pupil 5 of the eye 1. In one embodiment, the fundus 4 is imaged through 2 mm of central pupil diameter and only a fraction of the light scattered by the retina 2 is collected. Assuming that the retinal reflection represents a Lambertian source and assuming the maximum diameter of the eyeball at 30 mm, the total energy of light scattered by the retina is therefore $7.2 \times 10^{-5}$ Joules. The maximum reflectivity of the retina has been found to be approximately 10%, with an average of about 1 to 2%.

Thus, in one embodiment, at least about $7.2 \times 10^{-4}$ Joules (or about 0.5 lumen-seconds, assuming 683 lumens per watt conversion) of light may be provided incident onto the retina 2. Assuming a maximum exposure time of 10 milliseconds that prevents the blurring of the image due to shaking, the incident light onto the retina may be at least 0.072 Watts or 50 Lumens. If 1 milliseconds exposure time is used, then the minimum illumination power may be 0.7 W or 500 lumens. The minimum illumination requirement may be further increased if losses (reflections off lenses, poor fiber coupling, etc) are present in the optical system.

In one embodiment, visible bright LEDs may be used as the visible light source 40 for illumination. Multiple such LEDs may be used to achieve the necessary light levels in the fundus. In another embodiment, a xenon flash may be used as the visible light source 40.

In another embodiment, a supercapacitor-based LED flash may be used as the visible light source 40. In a further embodiment, a bundle of multiple supercapacitor-based LEDs may be used. In one embodiment, four such supercapacitor-based LEDs may be used. In another embodiment, the light source may be applied external to the device; for example the light may be transmitted from an external probe through the sclera, allowing the camera 10 to image the retina 2 through a small pupil so that the Gullstrand principal is not violated.

Figure 13A:
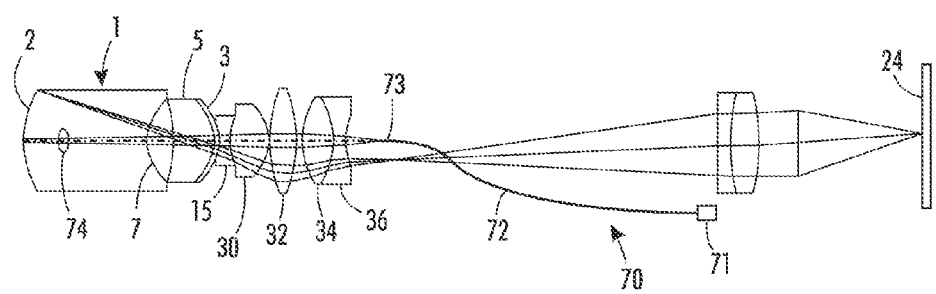
FIG. 13A is a schematic illustration of the optical system of a fundus camera including a first means for providing a fixation target.
Figure 13B:
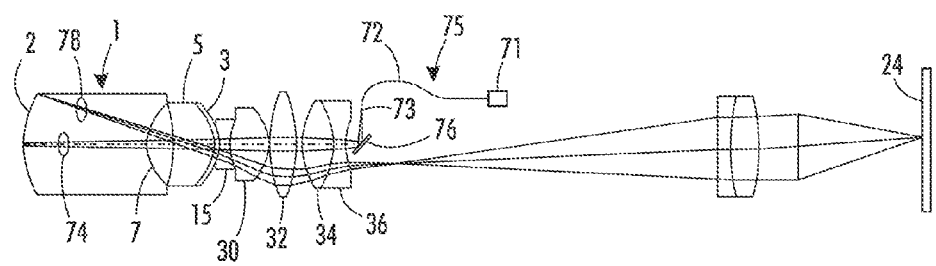
FIG. 13B is a schematic illustration of the optical system of a fundus camera including a second means for providing a fixation target.

In another embodiment, the camera 10 may be provided with means for providing a fixation target, such as the means shown in FIGS. 13A and 13B. A fixation target is a target for a patient to "look at" while the fundus imaging is being performed. By providing such a target, the patient's eye may be optimally aligned during the imaging, and the patient better holds his/her eye still while imaging. The target may be a small spot of light directed into the patient's eye prior to the fundus imaging.

Referring first to FIG. 13A, the fixation target is a spot of light from a target source 70. The target source 70 is comprised of a light source 71, such as a visible LED, and an optical fiber 72. The end 73 of the fiber 72 is centrally located and aligned so as to direct light rays 74 through the optics of the camera and onto the fundus of the eye in a small focused spot.

Referring to FIG. 13B, the fixation target is a spot of light from a target source 75. The target source 75 is comprised of a light source 71, an optical fiber 72, and a mirror 76. The mirror 76 is centrally located and positioned so as to reflect light from the end 73 of the fiber through the optics of the camera and onto the fundus of the eye in a small focused spot. The mirror reflects some of the light from the fixation target and transmits most of the light traveling along the device, i.e., the light traveling from the retina 2 (for example, the three rays 78 from a corner of the field of view on the retina 2), and onto the CCD sensor 24 to obtain an image of the fundus.

In a further embodiment (not shown), the camera 10 may be provided with an optical filter to reduce the red content of the image delivered to the CCD sensor 24. This results in a much less red image of the fundus having higher contrast. Fixturing may be provided in the camera 10 to make the filter removable therefrom, or movable linearly or rotatably into and out of position.

4. Image Analysis

The infrared illumination of the fundus is intended to automatically find the best focus setting, as well as the proper alignment of the camera 10 with the eye 1. Referring again to FIG. 1A, during the movement of the lens 21 by the focusing mechanism 18, a small frame of the video stream from the CCD 24 is analyzed by the on-board electronics 26. The analysis methods may include analyzing the spatial frequencies of the image using the discrete Fourier Transform. The amplitude of the high frequency components change as the focusing lens 21 moves. The focus of the lens 21 and position of the camera 10 that correspond to the maximum amplitude of the high spatial frequency components defines the best overall alignment and setting for image capture.

In addition to the spatial frequency analysis, the image may be checked electronically for the presence of the main fundus features, such as the optic nerve, fovea, branches of the central retinal vein and central retinal artery and, confirmation of the superior and inferior temporal arcades, for example. Once the main components of the image are identified and the best focusing is achieved, control logic provided in the electronics 26 concludes that the camera 10 is properly aligned, and starts the flash-aided image capture process. The image analysis software that is provided in the processor electronics 26 is sufficiently fast to perform the required analyses on the time scale which the camera user can hold the camera steady, and the patient's eye 1 can remain motionless. In summary, the camera 10 performs real-time or "on-the-fly" image processing for focusing and image selection using digital signal processing with the image processor 26.

While a full 40 degrees field of view unprocessed image may be provided in the camera 10, it places many conditions on the imaging system design, illumination requirements, pupil dilation and other. A smaller field of view may significantly simplify the imaging and illumination systems of the camera 10. In such an embodiment, the optical aperture and stop requirements are relaxed, illumination requirements are reduced by the square of the decrease in the FOV, and the image can be acquired through smaller pupils. All of these simplifications result in a smaller form factor, reduced parts count and lower manufacturing cost of the camera 10. Using image processing algorithms, the full FOV imaging may be achieved by stitching multiple smaller FOV images together as shown in FIG. 3B. Because of the relaxed illumination and resolution requirements, the smaller FOV images may be acquired at a video rate of 30 images/per second.

Thus, the acquisition of the complete fundus image may be performed in a short amount of time, comparable to the single-shot image acquisition time. The unique structure of the retina and the distinctive features thereof provide a suitable field for image stitching and reconstruction. In one embodiment, a hand-held portable fundus camera is provided which uses a mosaic, or stitched digital image to generate a quality 20 to 40 degree FOV (from 10 degrees to 70) of the optic nerve, macula, and central retinal artery and vein. These components, especially the vascular tree, of the image can also be used to guide the image stitching process. The software may also be provided with the capability to improve image quality by selecting sections that are in optimal focus, and to reduce aberrations and reflections in this stitching methodology.

To obtain the multiple images for compiling the mosaic image of the fundus, the user may move the camera slightly on the patient's eye 1 to align it with a different part of the fundus 4 and acquires one or more images thereof, such that the multiple images acquired overlap each other. However, this may irritate the patient's eye and cause discomfort. To address the problem of selecting different portions of the fundus of an eye without performing such motion of the camera 10 relative to the eye 1, the camera 10 may be provided with means for selecting a portion of the fundus to be imaged.

Figure 10:
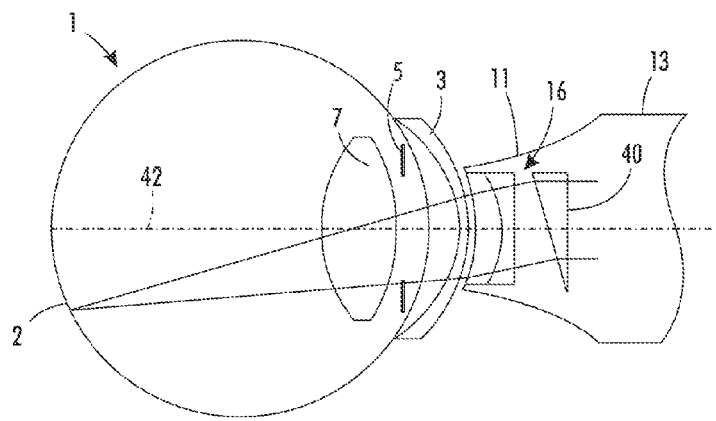
FIG. 10 is a cross-sectional schematic view of a first means for selecting a portion of the fundus to be imaged.

FIG. 10 is a cross-sectional schematic view of a first such means for selecting a portion of the fundus. A prism 40 is provided in the tip 11 of the camera 10. The prism 10 is held in a fixture (not shown) and may be separately rotatable around the central axis 42 by suitable means (not shown), such as a small piezo motor described previously herein. Alternatively, the tip 11 including the prism may be made rotatable. Mechanical settings may be provided to preferentially stop at several preset angular locations to obtain the full field of view. For the prism position shown in FIG. 10, the rays 44 depict the shifted location of the center of the field of view as a result of the prism 40. It can be seen that the field of view has been displaced from the visual axis 42 to a more peripheral location of the fundus 2. As the prism 40 is rotated relative to the eye 1, the peripheral areas of the fundus 2 are imaged. In that manner, the alignment of the camera 10 with respect to the eye 1 is maintained while the entire desired area of the fundus is imaged.

Figure 11:
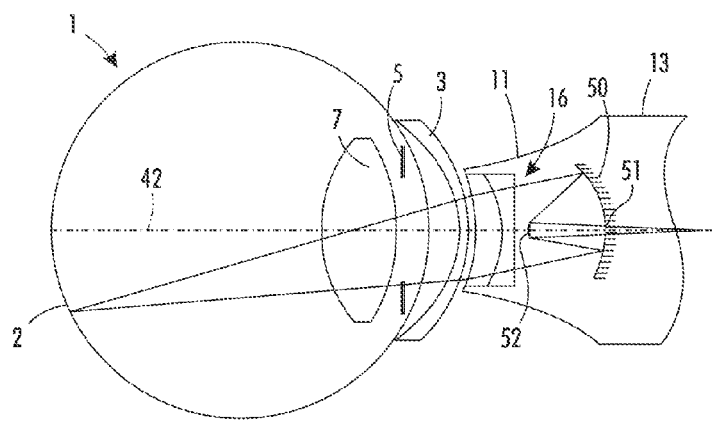
FIG. 11 is a cross-sectional schematic view of a second means for selecting a portion of the fundus to be imaged.

FIG. 11 is a cross-sectional schematic view of a second means for selecting a portion of the fundus to be imaged. Such means is comprised of two reflective elements 50 and 52, which are inserted in the optical system, and which form a tilted Cassegrain configuration. The first reflective element 50 defines the shift in the field of view, and the second reflective element 52 realigns the reflected light along the imaging axis 42 of the camera 10, through an opening 51 in the first reflective element 50.

The camera 10 may be supplied with either or both of the means depicted in FIGS. 10 and 11 contained in removable and interchangeable tips 11.

Figure 12:
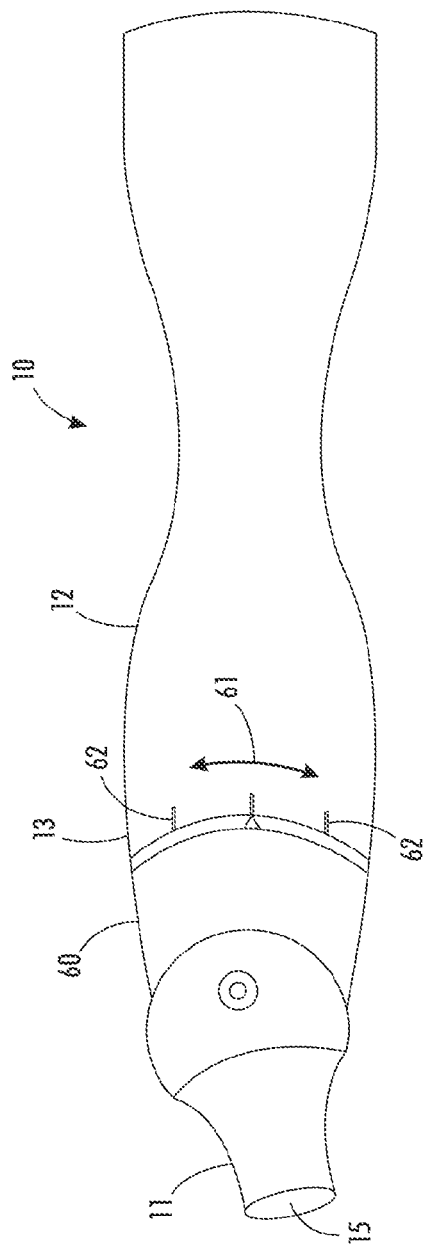
FIG. 12 is a perspective view of a fundus camera comprising a third means for selecting a portion of the fundus to be imaged.

FIG. 12 is a perspective view of a fundus camera comprising a third means for selecting a portion of the fundus to be imaged. The forward end 13 of the camera 10 may have the optics substantially as shown in FIG. 1, 4A, 8, or 9, but with the tip 11 being attached to the camera body 12 via a swivel fixture 60. The indexing of the imaging field of view may be accomplished by rotating the body 12 of the camera 10 with respect to the tip 11 and swivel fixture 60, as indicated by bidirectional arcuate arrow 61. Indicia 62 and mechanical notching (not shown) or other stops may be provided to preferentially stop the rotation at several preset angular locations to obtain the full field of view.

5. Power Supply and Consumption

The power supply of the camera 10 is preferably comprised of multiple batteries. In one embodiment, AA-sized NiMH rechargeable batteries may be used to power the camera. The AA form-factor allows for the use of alkaline batteries, which are widely available throughout the world. Presently, the capacity of a single NiMH AA battery may reach 3000 mAh. The alkaline batteries have similar capacities to the recharge batteries and may be used interchangeably. Power consumption of the fundus camera 10 may be comparable to that of a consumer digital camera.

The power consumption by a liquid lens (0.1 mW) as a focusing lens 21 may be over three orders of magnitude less than the power consumption by a piezo motor, such as a SQUIGGLE® motor (300 mW). Other mechanical actuators that may be used for focusing purposes may consume 50-100 milliwatt (mW) of power during motion. Typical consumption power of a CCD or CMOS array is 100 mW to 200 mW, while the digital signal processing by the image processing electronics 26 may require on average 200-300 mW of power. Flash visible light sources 40 (either xenon or supercapacitor LEDs) may require about 1 Watt of power consumption during the charging stage, which typically lasts about 2 seconds.

The fundus camera 10 may be configured to be used for a standard 8-10 hour work day, after which it may be recharged. According to the above specifications, in one embodiment, the peak power consumption may vary between approximately 1 W and 2 W depending whether the flash capacitor is charged. Since such a camera 10 would likely not be used continuously, and assuming 25% time usage at 1 W power consumption and the flash frequency of 50 times per hour, the average energy consumption would be 1150 J. Four nominal AA batteries hold 4×1.5 A×60 sec×3 V=1080 J of energy. Thus, four AA batteries may power such a camera 10 for up to 10 hours. Other small, high energy density batteries, such as those specifically made for digital camera use may be suitable to provide enough energy for a day's use, or longer.

6. Corneal Interface

The front contacting lens 15 of the fundus camera 10 is the part of the camera that interfaces with a living human eye. A smooth sterile disposable attachment 14 is preferably provided to cover the front contact lens 15. The disposable interface attachment 14 is preferably made from well known bio- and ophthalmic-compatible polymers, such as materials used in manufacturing intraocular lenses or hard or soft contact lenses. Examples of such materials are hydrogels, 2-hydroxyethyl methacrylate (HEMA), polymethyl methacrylate (PMMA), acrylic (including hydrophilic or hydrophobic acrylics), or silicone.

In one embodiment (not shown), in order to avoid uncomfortable pressure against or physical damage to the cornea 3, a safety mechanism minimizing external force may be built in to the camera 10. A spring type mechanical system and a force or pressure transducer may be integrated into the distal end 13 of the camera 10. The spring mechanism may hold the front contact lens 13 and may act as a cushion to prevent the damage to corneal endothelium and epithelium. The transducer measures the pressure with which the technician pushes the camera 10 onto the eye 1. If the pressure of contacting lens 15 of the camera 10 against the eye exceeds a safe level, a warning sound may be played, or other safety measures may be implemented. In addition, the force transducer may be used as a triggering device, which informs the camera 10 to begin the focus alignment algorithm and acquire a fundus image. Alternatively, a button (not shown) may activate the alignment/image capture algorithm. The eye protection system may further include an air, other gas and/or gel cushioning system whereby the cornea and eye are afforded protection through a deformable spacer. The deformable spacer may be a plastic or gel. The cushion system may be detachable and replaceable.

7. Laboratory Prototype Example

Figure 6:
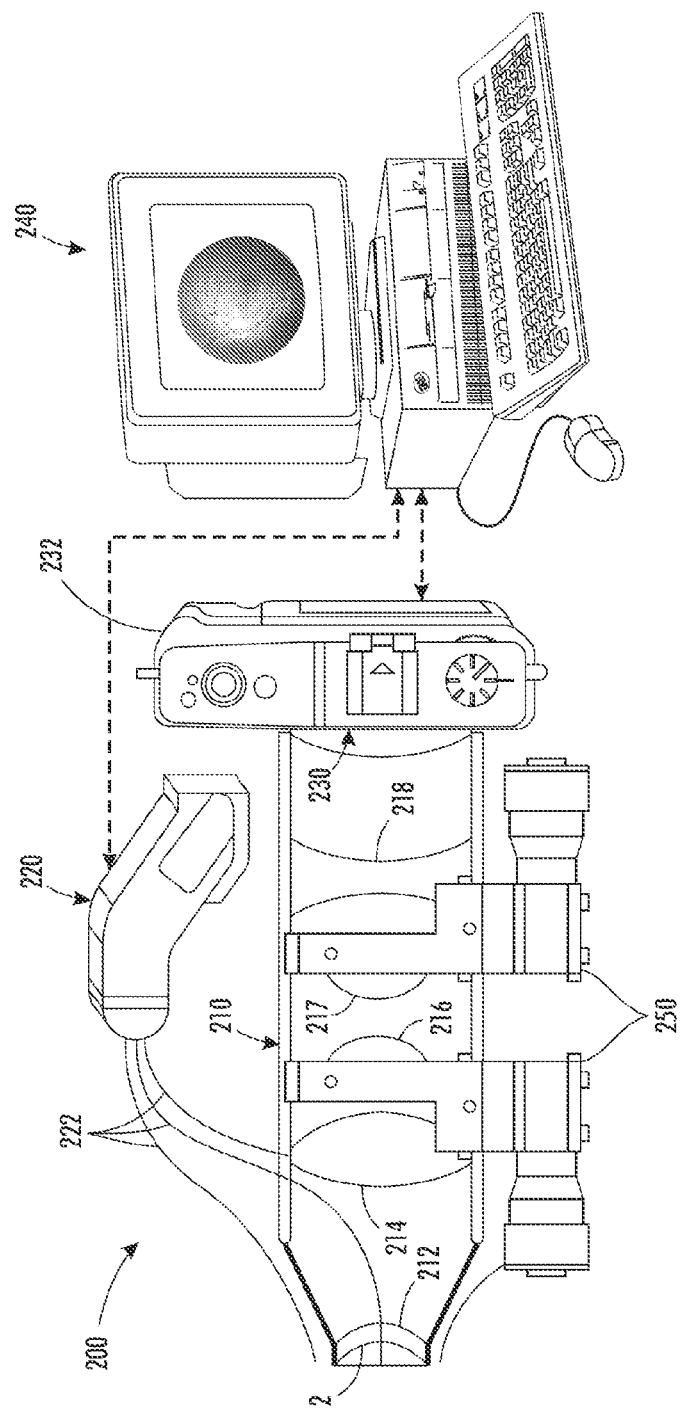
FIG. 6 depicts one embodiment of a prototype of the fundus camera.

FIG. 6 shows a simplified schematic of a prototype of a fundus camera 200 that may be constructed. The prototype fundus camera 200 may be comprised of a housing 210 containing imaging lenses 212, 214, 216, 217, and 218, an illumination system 220, a sensor array 230 and a computer 240.

The sensor array 230 may be provided as a CCD disposed in a consumer SLR camera 232. Alternatively, the camera 232 may be replaced by a smaller form-factor CCD sensor (not shown). The sensor 230 may be connected to an external power supply and acquisition electronics using flexible electric connections (not shown).

In the prototype embodiment depicted in FIG. 6, the illumination flash and continuous wave light sources are housed in the illumination system 220, which is outside the housing 210. A standard photographic flash unit may be coupled with the optical fiber bundle via a coupling adapter, containing optics that image a flash xenon tube to a smaller area and thus increase the coupling efficiency of the light into the fiber. Alternatively, a supercapacitor powered LED (not shown) may be implemented instead of a xenon flash light source. A separate housing may be used for coupling IR LEDs into the fiber for continuous infrared monitoring of the fundus. The light components are connected to the hand-held unit via multiple optical fibers 222. The ends of the fibers are integrated along the contact lens 212 as described previously.

The focus adjustments of the hand-held prototype 200 may be accomplished manually using micrometer actuators 250. Coarse focusing adjustment may be performed prior to the contact with the cornea 2 if the refractive error of the subject is known. This coarse focusing method may be performed by rotating lenses of differing power into the imaging axis. Thus, gross focus is set allowing for the device to work through narrower range of diopters during image acquisition. The lens location requirements corresponding to different levels of myopia and hyperopia may be calibrated using a model eye.

In another embodiment, the manually driven focus mechanisms 250 may be replaced by electronically controlled piezo motors. The focus adjustment may then be performed by the operator, or operator assistant, during the camera contact phase. The focusing process may be further automated by integrating the video image of the fundus into a feedback loop controlling the focusing mechanism.

The hand-held unit illumination components, imaging sensor and the focusing mechanism may be controlled by the computer 240. The control of the camera components, image acquisition, and image analysis may be performed using software.

7. Alternative Devices

Figure 7:
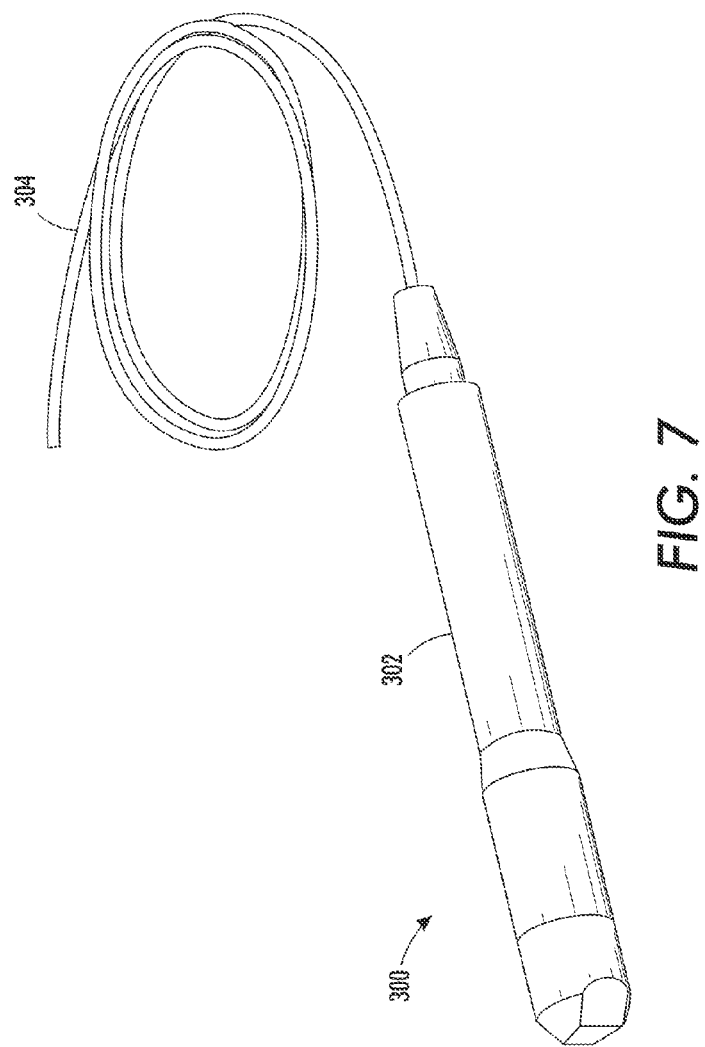
FIG. 7 is a B scan ultrasonic probe, which may be used for analyzing the retina with attachment to a portable computing platform such as an iPhone® attachment for medical use.

It is noted that other ophthalmic and medical imaging systems such as corneal topography, tomography, keratometry, pupillometry, aberrometry, pachymetry, and autorefraction may be miniaturized into a hand held device that interfaces with a hand held portable computing platform, such as an iPhone® or Android™. By way of illustration, FIG. 7 is a B scan ultrasonic probe, which may be used for analyzing the retina with attachment to a portable computing platform such as an iPhone® attachment for medical use. The ultrasonic probe 300 may include ultrasonic image processing electronics (not shown), a power supply (not shown), and wireless signal transmission electronics (not shown), within the probe body 302 in a manner similar to that described for the fundus camera 10 of FIG. 1A. Alternatively, the ultrasonic probe 300 may be in signal communication with a PC, iPhone®, or Android™ through a cable 304 and a connector (not shown).

It is, therefore, apparent that there has been provided, in accordance with the present invention, a compact portable fundus camera. Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims.

We claim:

1. A camera for imaging the fundus of an eye, the camera comprising optics aligned along an imaging axis intersecting a point on the fundus and configured to focus light reflected back from the fundus onto an image receptor, wherein the optics are capable of varying a field of view of the camera along a path circumferentially around the point on the fundus, whereby the image receptor acquires images of portions of the fundus located at different peripheral locations around the point of the fundus.

2. The camera of claim 1, wherein the optics are comprised of a prism rotatable around the axis to vary the field of view along the path circumferentially around the point on the fundus.

3. The camera of claim 1, wherein the optics are comprised of first and second reflective elements arranged in a Cassegrain configuration to vary the field of view along the path circumferentially around the point on the fundus.

4. The camera of claim 1, wherein a portion of the optics are contained in a swivel fixture to vary the field of view along the path circumferentially around the point on the fundus.

5. The camera of claim 1, further comprising a housing comprising an internal cavity terminating at a forward housing end, a forward lens, and a light source configured to direct light from locations distributed around the perimeter of the forward lens forwardly out of the housing end, wherein the forward lens is suspended in the housing on a cushioning mount and is rearwardly displaceable by contact with the eye.

6. The camera of claim 5, further comprising a sensor that detects pressure of the forward lens against the eye.

7. The camera of claim 1, further comprising a fixation target source comprised of a light source and an optical fiber configured to direct light from the light source through the optics and focus the light on a spot on the fundus.

8. A camera for imaging the fundus of an eye, the camera comprising a housing comprising an internal cavity terminating at a forward housing end, a forward lens aligned along an imaging axis intersecting a point on the fundus, a light source configured to direct light from locations distributed around the perimeter of the forward lens forwardly out of the housing end, and means for selecting a portion of the fundus to be imaged from among a plurality of portions located along a circumferential path around the point on the fundus.

9. A method of imaging the fundus of an eye comprising:
   a) contacting a camera with the cornea of the eye;
   b) directing light from locations distributed around the perimeter of a forward lens of the camera forwardly out of a housing end of the camera through the pupil of the eye and onto a first portion of the fundus located along a circumferential path around a point on the fundus intersected by an imaging axis of the camera;
   c) receiving light reflected back from the first portion of the fundus onto an image receptor in the camera;
   d) directing light from locations distributed around the perimeter of the forward lens of the camera through the pupil of the eye and onto a second portion of the fundus located along the circumferential path around the point on the fundus;
   e) receiving light reflected back from the second portion of the fundus onto the image receptor in the camera; and
   f) processing data from the image receptor to create a digital image of the fundus.

10. The method of claim 9, further comprising directing a focused spot of light as a fixation target onto the fundus of the eye.

11. The camera of claim 1, wherein the optics are comprised of a focusing mechanism comprising a liquid lens.

12. The method of claim 9, further comprising using a liquid lens to focus the image of the fundus.

* * * * *